United States Patent
Williamson (10) Patent No.: US 9,618,440 B2
(45) Date of Patent: *Apr. 11, 2017

(54) GAS DETECTOR FOR USE WITH AN AIR SAMPLING PARTICLE DETECTION SYSTEM

(71) Applicant: Xtralis Technologies Ltd, Nassau, NP (BS)

(72) Inventor: Alasdair James Williamson, Worthing (GB)

(73) Assignee: Xtralis Technologies Ltd, Nassau (BS)

( * ) Notice: Subject to any disclaimer, the term of this patent is extended or adjusted under 35 U.S.C. 154(b) by 0 days.

This patent is subject to a terminal disclaimer.

(21) Appl. No.: 14/931,339

(22) Filed: Nov. 3, 2015

(65) Prior Publication Data

US 2016/0054215 A1 Feb. 25, 2016

Related U.S. Application Data

(63) Continuation of application No. 13/376,273, filed as application No. PCT/GB2010/050938 on Jun. 3, 2010, now Pat. No. 9,235,970.

(30) Foreign Application Priority Data

Jun. 5, 2009 (AU) ................................ 2009902606

(51) Int. Cl.
 *G08B 17/117* (2006.01)
 *G01N 37/00* (2006.01)
 (Continued)

(52) U.S. Cl.
 CPC ....... *G01N 15/0656* (2013.01); *G08B 17/117* (2013.01); *G08B 21/14* (2013.01);
 (Continued)

(58) Field of Classification Search
 CPC . F24F 2011/0026; G08B 17/117; Y02B 30/78
 See application file for complete search history.

(56) References Cited

U.S. PATENT DOCUMENTS 3,559,491 A * 2/1971 Thoen .................. G01N 1/2258
 73/863.21
4,019,863 A 4/1977 Jenkins et al.
 (Continued)

FOREIGN PATENT DOCUMENTS

EP 1772719 A1 4/2007
FR 2670010 A1 6/1992
 (Continued)

OTHER PUBLICATIONS

"U.S. Appl. No. 13/376,273, Final Office Action mailed Apr. 24, 2015", 11 pgs.
 (Continued)

*Primary Examiner* — Lisa Caputo
*Assistant Examiner* — Punam Roy
(74) *Attorney, Agent, or Firm* — Schwegman Lundberg & Woessner, P.A.

(57) ABSTRACT

An apparatus and methods for detecting the presence of gases is described. The gas detection apparatus includes, a housing adapted to be in fluid communication with a duct of a particle detection system, and at least one gas detector sensitive to a target species arranged in fluid communication with the housing to detect the presence of the target species in at least part of the air sample flowing in a duct. In one form the gas detection apparatus forms part of a system for detecting a condition in an environment that includes, a particle detector; a duct system in fluid communication with the environment and the particle detector and an aspirator to draw an air sample flow from the environment to the particle detector.

21 Claims, 6 Drawing Sheets

(51) Int. Cl.
*G01N 15/06* (2006.01)
*G08B 21/14* (2006.01)
*G08B 29/22* (2006.01)
*F24F 11/00* (2006.01)

(52) U.S. Cl.
CPC ...... *G08B 29/22* (2013.01); *F24F 2011/0026* (2013.01); *F24F 2011/0027* (2013.01); *F24F 2011/0028* (2013.01); *F24F 2011/0032* (2013.01); *Y02B 30/78* (2013.01)

(56) References Cited

U.S. PATENT DOCUMENTS

| | | | |
|---|---|---|---|
| 4,257,258 A | 3/1981 | Bovenlander | |
| 4,279,142 A * | 7/1981 | McIntyre | G01N 33/0006 73/1.06 |
| 4,856,352 A * | 8/1989 | Daum | G01N 1/2247 73/1.06 |
| 5,103,212 A * | 4/1992 | Notarianni | G08B 17/10 340/628 |
| 5,477,218 A * | 12/1995 | Manmoto | G08B 17/107 250/574 |
| 5,844,148 A * | 12/1998 | Klein | G01N 1/2226 73/863.82 |
| 5,959,188 A * | 9/1999 | Deutsch | G01N 33/0006 340/515 |
| 6,285,291 B1 | 9/2001 | Knox et al. | |
| 6,425,297 B1 * | 7/2002 | Sharp | G01N 1/26 73/863.33 |
| 6,470,732 B1 | 10/2002 | Breton | |
| 6,741,181 B2 | 5/2004 | Skaggs | |
| 6,769,285 B2 | 8/2004 | Schneider et al. | |
| 6,985,081 B2 * | 1/2006 | Wagner | G08B 17/10 169/60 |
| 7,375,642 B2 * | 5/2008 | Siemens | G08B 17/10 340/628 |
| 7,661,290 B2 * | 2/2010 | Gu | G01N 33/0006 73/1.01 |
| 7,954,390 B1 | 6/2011 | Andrews, Jr. et al. | |
| 8,087,307 B2 * | 1/2012 | Gauthier | G01N 1/2202 73/863.23 |
| 8,412,481 B2 * | 4/2013 | Knox | G01N 1/26 701/100 |
| 9,235,970 B2 | 1/2016 | Williamson | |
| 2007/0008157 A1 * | 1/2007 | Siemens | G08B 17/10 340/577 |
| 2007/0084286 A1 * | 4/2007 | Ajay | G01F 1/667 73/597 |
| 2007/0168140 A1 | 7/2007 | Knox | |
| 2007/0214862 A1 * | 9/2007 | Kubinski | F01N 13/008 73/1.06 |
| 2010/0194575 A1 * | 8/2010 | Rodriguez | G08B 29/145 340/628 |
| 2012/0079871 A1 | 4/2012 | Williamson | |

FOREIGN PATENT DOCUMENTS

| | | |
|---|---|---|
| GB | 1509361 | 5/1978 |
| GB | 2121180 A | 12/1983 |
| GB | 2347541 A | 9/2000 |
| JP | 60063454 A | 4/1985 |
| JP | 07182583 | 7/1995 |
| JP | H07334780 | 12/1995 |
| JP | 09269283 | 10/1997 |
| JP | 2003156463 | 5/2003 |
| WO | WO-2007/095675 A1 | 8/2007 |
| WO | WO-2008/109933 A1 | 9/2008 |
| WO | WO-2010/043272 A1 | 4/2010 |

OTHER PUBLICATIONS

"U.S. Appl. No. 13/376,273, Final Office Action mailed May 21, 2014", 9 pgs.

"U.S. Appl. No. 13/376,273, Final Office Action mailed Oct. 2, 2014", 13 pgs.

"U.S. Appl. No. 13/376,273, Non Final Office Action mailed Jan. 15, 2015", 14 pgs.

"U.S. Appl. No. 13/376,273, Non Final Office Action mailed Oct. 4, 2014", 8 pgs.

"U.S. Appl. No. 13/376,273, Notice of Allowance mailed Aug. 4, 2015", 10 pgs.

"U.S. Appl. No. 13/376,273, Response filed Feb. 12, 2014 to Non Final Office Action mailed Oct. 4, 2013", 14 pgs.

"U.S. Appl. No. 13/376,273, Response filed Apr. 6, 2015 to Non Final Office Action mailed Jan. 15, 2015", 17 pgs.

"U.S. Appl. No. 13/376,273, Response filed Jun. 23, 2015 to Final Office Action mailed Apr. 24, 2015", 17 pgs.

"U.S. Appl. No. 13/376,273, Response filed Jul. 21, 2014 to Final Office Action mailed May 21, 2014", 15 pgs.

"U.S. Appl. No. 13/376,273, Response filed Dec. 2, 2014 to Final Office Action mailed Oct. 2, 2014", 19 pgs.

"Australian Application No. 2009902606, International-Type Search Report mailed Feb. 26, 2010", (Feb. 26, 2010), 2 pgs.

"European Application Serial No. 10727127.2, Summons to Attend Oral Proceedings mailed Oct. 13, 2015", 5 pgs.

"International Application No. PCT/GB2010/050938, International Search Report and Written Opinion mailed Aug. 6, 2010", (Aug. 16, 2010), 10 pgs.

"Japanese Application No. 2012-513684, Non-Final Office Action with English translation", (2013), 5 pgs.

"U.S. Appl. No. 13/376,273, Corrected Notice of Allowance mailed Dec. 15, 2015", 2 pgs.

* cited by examiner

GAS DETECTOR FOR USE WITH AN AIR SAMPLING PARTICLE DETECTION SYSTEM

PRIORITY CLAIM TO RELATED APPLICATIONS

This application is a continuation application of and claims the benefit of priority to U.S. patent application Ser. No. 13/376,273, filed on Dec. 5, 2011, which is a U.S. national stage application under 35 U.S.C. §371 of PCT/GB2010/050938, filed Jun. 3, 2010, and published as WO 2010/140001 on Dec. 9, 2010, which claims priority to Australian Application No. 2009902606, filed Jun. 5, 2009, which applications and publication are incorporated herein by reference and made a part hereof in their entirety, and the benefit of priority of each of which is claimed herein.

FIELD OF THE INVENTION

The present invention relates to detecting a condition in the environment. In particular, the invention relates to an apparatus and methods for detecting the presence of gases. Preferably, the invention relates to an apparatus and methods for detecting gases indicative of a threat, for instance a gas leak or a fire.

BACKGROUND OF THE INVENTION

Gas detectors are used to detect the presence, and measure the concentration of, gases or other volatile compounds. Among other uses, they may be employed in a monitoring system to, for instance, detect the presence of (i) a toxic gas (e.g. (a) ammonia released in an enclosed space, (b) carbon dioxide or carbon monoxide produced from a controlled fire event such as fuel fired furnaces, gas hot water heaters, gas stoves, gas dryers, space heaters, charcoal grills, fireplaces, vehicles (including build-up in carparks), and lawn movers, and (c) methyl isocyanate gas accidentally released from an industrial manufacturing plant);

(ii) a flammable gas leak (in an effort to prevent fire), or flammable gas build-up (e.g. methane in sewage systems); and/or (iii) a gas or other volatile compound that is indicative of an impending fire (i.e. smoldering or melting materials) or pre-existing fire (i.e. burning materials) or the nature of a fire (e.g. the type of material that is burning).

Although in this specification the gas detector will be predominantly described in relation to the latter (i.e. the prevention and detection of an undesirable fire event) for ease of understanding, this should not limit the scope of the invention. Clearly, a gas detector is also useful in other situations.

It is an object of the present invention to provide an improved gas detector apparatus. In some aspects, the present invention seeks to provide an improved gas detector apparatus that incorporates or can be used in conjunction with a smoke detector. In some aspects, the present invention seeks to provide an improved gas detector apparatus that can be used in conjunction with air sampling pollution monitoring equipment such as an aspirated smoke detector with an associated sampling pipe network.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In a first aspect there is provided a gas detection apparatus for use with an air sampling particle detection system of the type including a duct in which an air sample flows and a particle detector for analyzing at least a portion of the air sample flowing in the duct, the gas detection apparatus including: a housing adapted to be in fluid communication with a duct of the particle detection system, and at least one gas detector sensitive to a target species arranged in fluid communication with the housing to detect the presence of the target species in at least part of the air sample flowing in the duct.

Preferably the housing of the gas detection apparatus includes a duct portion configured to be interposed in a duct of a particle detection system in use. Advantageously this allows retrofitting of the gas detection apparatus to an existing sampling duct of a particle detection.

The gas detection apparatus can further include: an inlet port arranged to draw a sub-sample from the air sample flowing in the duct of the particle detection system, or duct portion of the housing, for analysis by the gas detection apparatus; an outlet port arranged to exhaust the sub-sample of air; and a flow path extending from the inlet port to the outlet port, and at least one gas detector sensitive to a target species arranged in fluid communication with the flow path to detect the presence of the target species in the sub-sample.

The sensing apparatus further includes: a sample passage defining the flow path; a test region; at least one membrane providing fluid communication between the sample passage and the test region such that a target species in the sample is capable of passing through the membrane and into the test region. In this case the sample passage can include a flow control structure to direct at least a portion of the sample gas towards the membrane.

The flow control structure can advantageously define a curve in the sample passage and the membrane can be located on an outside portion of the curve.

The flow control structure can include any one or more of:
(i) a narrowing of the sample passage;
(ii) a bulbous protrusion from a surface defining a wall of the sample passage;
(iii) a baffle extending into the sample passage from at least one of the surface defining the sample passage; and
(iv) an object within the sample passage obstructing the sample flow.

Preferably the inlet port includes a flow directing element extending into the duct of the particle detection system or duct portion of the housing to direct a sub-sample from the air sample into the sample passage. Most preferably the flow directing element is concave-shaped.

The outlet port is preferably also in fluid communication with the duct, such that the sub-sample is returned to the air sample flow in the duct of the particle detection system.

In a preferred form, the inlet port and outlet port are positioned in the airflow in the duct such that a pressure drop in the duct between the inlet port and outlet port serves to draw air through the flow path.

The gas detection apparatus can further includes means to draw air into the input port, for example a fan, or pump can be provided.

The gas detection apparatus can further include a secondary gas inlet configured to provide a calibration gas to the test region. Preferably gas provided by the secondary gas inlet to the test region is flushed from the test region through one or more associated membranes into the flow path.

In some embodiments, the gas detection apparatus can include a particle detection apparatus arranged to detect the presence of particles in the flow path. The particle detection apparatus is preferably a nephelometer arranged to transmit a beam of light across the airflow path of the case detection device.

In a preferred embodiment, the flow path of the gas detection apparatus does not include a particle filter.

Some embodiments of the gas detection apparatus can include any one or more of: an explosion proof housing; one or more flame arrestors; intrinsically safe electrical circuitry. Some embodiments of the gas detection apparatus can be intrinsically safe.

In another aspect, the present invention provides a system for detecting a condition in an environment including: a particle detector; a duct system in fluid communication with the environment and the particle detector; an aspirator to create a draw an air sample flow from the environment to the particle detector; and at least one gas detection apparatus of the type described herein.

Most preferably each gas detection apparatus forms a dedicated module. The dedicated module is preferably adapted for placement as part of the duct system of the particle detection system. Most preferably the gas detection apparatus is positioned on the duct system upstream of a particle detector.

In a preferred form, the gas detection apparatus can be arranged to draw a sub-sample from the air sample prior to introduction of the air sample to the particle detector. It can also be arranged to return the subsample to the duct system, rather than exhausting it to atmosphere. In situations where the gas detection system is located upstream of the particle detector this approach can advantageously minimize pressure losses in the air sampling duct and/or minimize transport time delays potentially caused by the gas detection apparatus.

Alternatively, the gas detection apparatus is arranged to draw a sub-sample from the air sample after the air sample has been exhausted from the particle detector.

Preferably the duct system includes at least one air sampling pipe including a plurality of air sample inlets arranged in series along the duct, and the gas detection apparatus being arranged to take a sub-sample from the air sampling pipe downstream of at least two air sample inlets and being calibrated with a dilution factor reflecting a diluting effect of the plurality of sample inlets on the air sampling pipe upstream of the gas detection apparatus.

In some embodiments the system includes at least two gas detection apparatuses. In this case each gas detection apparatus can be arranged to take a sub-sample from an air sampling pipe at a respective position and be calibrated with a corresponding dilution factor reflecting a diluting effect of the sample inlets of the air sampling pipe upstream of the gas detection apparatus's respective position.

In a system in which the duct system includes at least two air sample inlets arranged to draw air samples from respective portions of the environment, the system can further include at least two gas detection apparatuses being sensitive to at least one target species to be detected in an portion of the environment proximate the a respective air sample inlet.

In the above systems at least two gas detection apparatuses can be positioned with respect to the duct system such that each is able to draw a sub-sample from the duct including an air sample flow drawn from a corresponding subset of air sample inlets which are not the same. In this case, the subset of air sample inlets corresponding to one gas detection apparatus may differ by at least one air sample inlet to the subset of air sample inlets of another particle detection apparatus. The subset of air sample inlets corresponding to one gas detection apparatus may not include any air sample inlets that form part of the subset of air sample inlets corresponding to another particle detection apparatus.

In exemplary systems with multiple gas detection apparatuses, at least two gas detection apparatuses can be sensitive to at least one different target species.

In some systems the gas detection apparatus can be intrinsically safe. The particle detector, or any (or possibly all) component of the system can also be intrinsically safe.

The system can include a barrier device for providing electrical power to either or both of the intrinsically safe particle detector or intrinsically safe gas sensing apparatus, or any other component of the system.

The inventors have found that, in a gas detector apparatus including a detector test region that is separated from a gas sample region by a membrane, the inclusion of a flow control structure to direct at least a portion of the gas being sampled towards the membrane results in improvement of the gas detector apparatus. Accordingly, in a further aspect of the invention there is provided a gas detector apparatus for detecting the presence of a target species within a bulk gas, the gas detector apparatus including a sample inlet a sample passage through which a sample gas flows from the sample inlet, the sample gas being at least a portion of the bulk gas;

a test region;

at least one membrane for providing fluid communication between the sample passage and the test region such that a target species in the sample is capable of passing through the membrane and into the test region; and at least one gas detector sensitive to the target species in fluid communication with the test region;

wherein the sample passage includes a flow control structure to direct at least a portion of the sample gas towards the membrane.

In another aspect of the invention there is provided a method for detecting the presence of a target species within a bulk gas in a gas detector apparatus, the method including the steps of drawing a sample gas through a sample inlet and into a sample passage, the sample gas being at least a portion of the bulk gas;

allowing at least the target species to pass into a test region through at least one membrane providing fluid communication between the sample passage and the test region; and testing for the presence of the target species in the test region using at least one gas detector in fluid communication with the test region;

wherein the method include directing at least a portion of the sample gas towards the membrane by a flow control structure in the sample passage.

Sample gas flowing in the sample passage will have at least a first flow direction (i.e. a first net direction). As will be discussed further, in some embodiments the flow control structure will cause the sample gas flowing in the sample passage to have at least a second flow direction. This second flow direction may refer to only a portion of the sample gas flow, a substantial portion of the sample gas flow, or essentially all of the sample gas flow (i.e. a second net direction).

The flow control structure may be the surface(s) defining the sample passage (as opposed to a distinct structure). In some embodiments the sample passage is shaped such that the sample gas changes its net flow direction from the first flow direction to a second flow direction, in these embodiments the membrane can be placed such that the first flow direction will be directed towards it. For example the flow control structure can define a bend or curve in the pipe with a membrane placed on the outside of the bend or curve.

In other embodiments, the first flow direction is not towards the membrane. In these embodiments, the sample passage includes a deflector as the flow control structure and the cross-sectional profile of the sample passage changes along its length. The deflector may be (i) integral with, (ii) attached to, or (iii) separate from the surface(s) defining the sample passage. In these embodiments, the surface(s) defining the sample passage result in the sample gas having a first flow direction, while the deflector causes at least a portion of the sample gas to be redirected to have at least a second flow direction that is towards the membrane. The deflector is necessarily proximal to the membrane such that at least some of the redirected sample gas contacts the membrane.

Preferably, the deflector is a surface or object that is aligned such that the second flow direction is towards the membrane. In these embodiments, the deflector is angled with respect to the membrane (i.e. not parallel to the surface of the membrane that is in the sample passage). Preferably, the deflector is inclined towards, rather than away from, the membrane. For example, the deflector may be (i) a smooth or sudden narrowing/constriction of the surface(s) defining the sample passage or (ii) a bulbous protrusion from a surface defining the sample passage ((i) and (ii) are examples of integral deflectors), (iii) a flat or curved baffle extending from at least one of the surface(s) defining the sample passage (as an example of an attached deflector), or (iv) an object (such as a bead) within the sample passage but not connected to the surface(s) defining the sample passage that is obstructing the sample flow (as an example of a deflector separate from the surface(s) defining the sample passage).

Preferably, the deflector is a surface that narrows the sample passage such that the volume through which the sample gas flows past the membrane is reduced. Without wishing to be bound by theory, this narrowing leads to an increased velocity and is thought to also lead to an increase in the turbulent nature of the sample gas flow in that region. Concomitant with the increased turbulence (and velocity) is an increase in the momentum flux/convection of the sample gas molecules towards the surface(s) defining the sample passage and towards the membrane. That is, an amount of sample gas molecules flowing in a first flow direction prior to entering the constriction will be caused to flow in a second flow direction towards the membrane by the narrowing (however this amount is likely to be small compared with the amount of sample gas molecules that remain flowing in the first flow direction). It is believed that this increase in the amount and speed of sample gas molecules being directed towards the membrane results in (a) a higher number of sample gas molecules passing through the membrane to the test region and (b) faster diffusion of sample gas molecules through the membrane and into the test region. These factors, respectively, lead to a gas detector apparatus that can detect an undesirable fire event sooner by having a lower activation threshold (i.e. a less advanced fire can be detected) and a faster response time (i.e. alarm lag time due to inherent slowness in the gas detector apparatus is reduced).

As well as narrowing the sample passage to increase turbulence and hence direct more sample gas molecules towards the membrane, it is preferable that the deflector also more overtly targets the sample gas flow towards the membrane. That is, the deflector is preferably such that a substantial portion of sample gas molecules originally flowing in a first flow direction are redirected to have a second flow direction that is towards the membrane. For example, the deflector may be a flat or curved surface extending from the surface(s) defining the sample passage, or a separate object, for example a rectangular prism, triangular prism, or semi-cylinder, positioned across the first flow direction of the sample gas to result in a disturbance to that flow and the second flow direction towards the membrane. That is, the flow of sample gas molecules is deflected/redirected/perturbed/disrupted by the deflector and forced to flow towards the membrane.

The gas detector apparatus of the present invention also includes a sample inlet in fluid communication with the sample passage. The sample inlet is also necessarily in fluid communication with the bulk gas. Preferably, the sample inlet is positionable within a flow of the bulk gas in a bulk gas duct. In these embodiments, the sample inlet is adapted to direct the flow of the bulk gas into the sample passage. This is preferably achieved by a sample inlet that is concave-shaped (with respect to the direction of flow of the bulk gas). For instance, the sample inlet is scoop-shaped. Typical flow rates for the bulk gas are up to about 120 L/min. Alternatively, bulk gas may be fed into the sample inlet. In these embodiments, a pump/fan/blower may be provided to direct the bulk gas into the sample inlet. In either case, desirable flow rates for the sample gas within the sample passage range from about 1 L/min to about 5 L/min.

The gas detector apparatus of the present invention preferably also includes a sample outlet in fluid communication with the sample passage. The sample outlet may be the same entity as the sample inlet, but is preferably different. More preferably, the sample outlet is in fluid communication with the bulk gas such that sample gas that has passed through the gas detector apparatus may be returned to its original source. In this case, the sample outlet is adapted to direct the sample gas into the flow of the bulk gas.

Membranes are often used in gas detectors for filtering interference elements (eg dust) and for allowing dilution of the sample gas/target species. The membrane is made of any suitable material as would be known in the art. For instance, the membrane may be polytetraflourethylene (e.g. Gore-tex) or Zitex. Preferably, the membrane is Gore-tex. The membrane must be porous to allow sample gas and target species to pass through to the test region and the gas detector. The dimensions of the membrane can be any that allow a sufficient amount of sample gas and target species to pass through (so that their concentration in the test gas is above the detection limit), and allow their passage within an acceptable timeframe (e.g. quickly for application in detection of an undesirable fire event). Preferably, the amount of sample gas and target species that is capable of passing through the membrane is significantly below the detector saturation point so that gas detector replacement is required less often. Suitable properties are pore sizes from about 4 micron to about 20 micron, and membrane thickness from about 0.28 millimeters to about 0.56 millimeters, although the invention should not be limited by this feature. There may be more than one membrane.

The test region of the gas detector apparatus contains a test gas, i.e. gas that is in direct contact with the detector(s). During normal operation of the gas detector apparatus, the test gas will be sample gas that has passed through the membrane from the sample passage. However, for the purposes of calibration, the test gas will be a calibration gas (such as known in the art). Calibration gas will be injected into the test region so that all the sample gas in the test region is pushed out through the membrane(s) back into the sample channel, this process effectively provides for back-flushing of the membrane to clear it of any debris, and (ii) calibration of the detector (when the test gas is a calibration gas). Back-flushing and calibration may be user-controlled, programmable intermittent or auto-responsive to operation conditions. The skilled person would understand the frequency at which back-flushing is required and at which calibration should be conducted.

There may be more than one gas detector and/or type of detector. Preferably, there are two gas detectors. Each gas detector may have its own associated deflector and/or membrane, or may share a common deflector and/or membrane.

In order to maximize response times and detection limits, the gas detector is preferably positioned in proximity to the membrane. Likewise, the deflector is preferably positioned in proximity to the membrane.

The gas detector apparatus may be operated in conjunction with a particle detector of any type known in the art, e.g. an aspirating smoke detector. Alternatively, a particle detector may be included within the gas detector apparatus of the present invention. In any case, the smoke and gas detector is preferably able to access a bulk gas obtained via air sampling pollution monitoring equipment such as a sampling pipe network. In such a case, the bulk gas can be pre-filtered for particulates prior to entering the sample inlet.

Accordingly, in a further aspect of the invention there is provided a sensing system for detecting an abnormal condition in an air volume, the sensing system including a particle detection stage and a gas detection stage in fluid communication with the air volume. The gas detection stage is preferably of the type described herein. The particle detection stage preferably includes an optical smoke detector, for example such as a VESDA particle detector supplied by Xtralis Pty Ltd. Preferably the sensing system is maintained in fluid communication with the air volume by an air sampling network.

BRIEF DESCRIPTION OF THE DRAWINGS/FIGURES

Exemplary embodiments of the present invention will now be described by way of non-limiting example only with reference to the accompanying drawings, which illustrate.

DETAILED DESCRIPTION OF THE EMBODIMENTS

The present invention will be best understood by reference to the following detailed description of the presently preferred embodiments.

Figure 1:
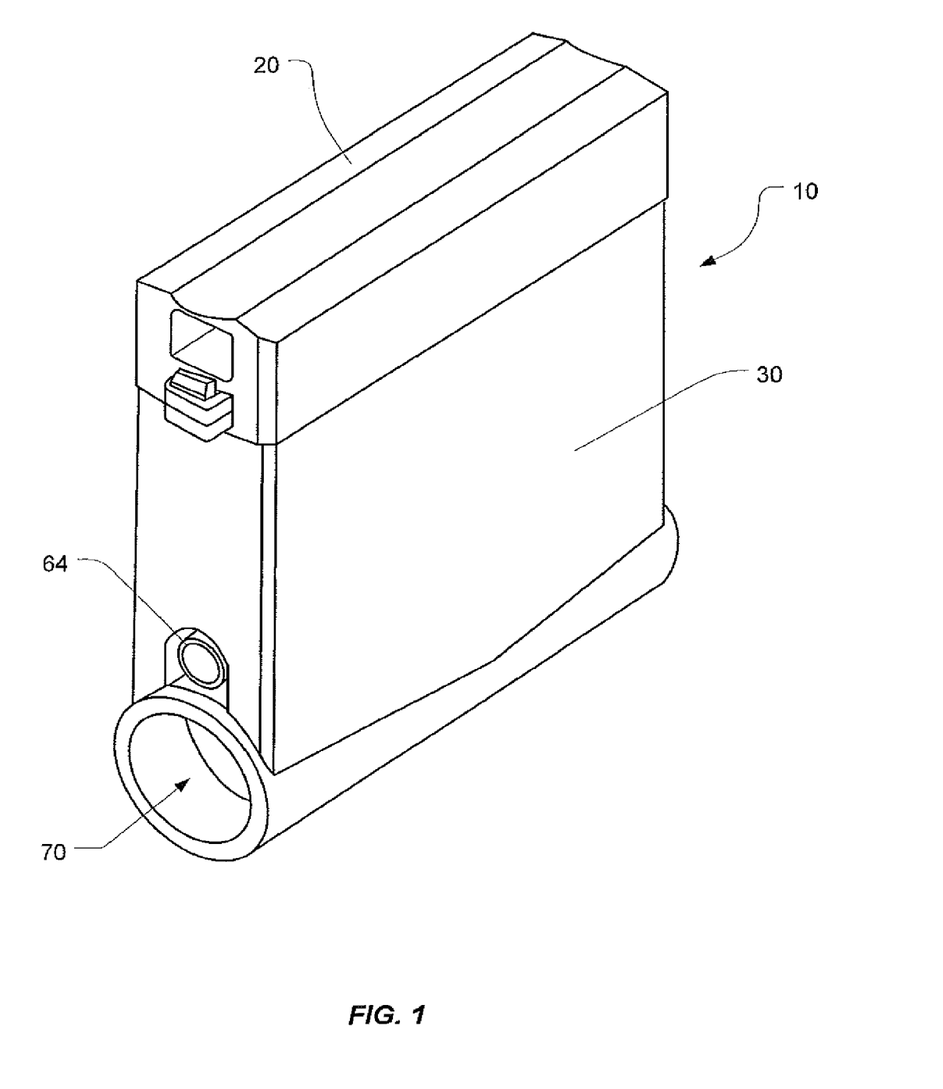
FIG. 1 illustrates an embodiment of the present invention showing the gas detector apparatus positioned on a bulk gas duct.

FIG. 1 shows an exterior view of the gas detector apparatus 10. The gas detector apparatus 10 has a lower main housing 30 and a lid compartment 20. The lower end of the main housing 30, defines a duct 70 into which bulk gas can be received. In use the bulk gas duct 70 can be connected to a source of bulk gas, e.g. a pipe forming part of a sampling network of an aspirated particle detection system, an inlet or exhaust of a particle detector, a gas delivery probe in fluid communication with a duct of an HVAC system or other air source, or simply placed in fluid communication with a volume of air being monitored for the target species.

The bulk gas is introduced into the duct 70 such that a gas detector(s) within the gas detector apparatus 10 can sense the level of one or more target species in the bulk gas or a subsample taken therefrom. A test or calibration gas can be input into test region 62 for calibration of the gas detectors housed in the apparatus 10 and for back flushing filter membranes of the apparatus 10.

As will be understood the system can include a communications interface, e.g. USB, Ethernet, etc. to enable communication with other systems, e.g. a fire alarm system, building monitoring, HVAC, etc.

Figure 2:
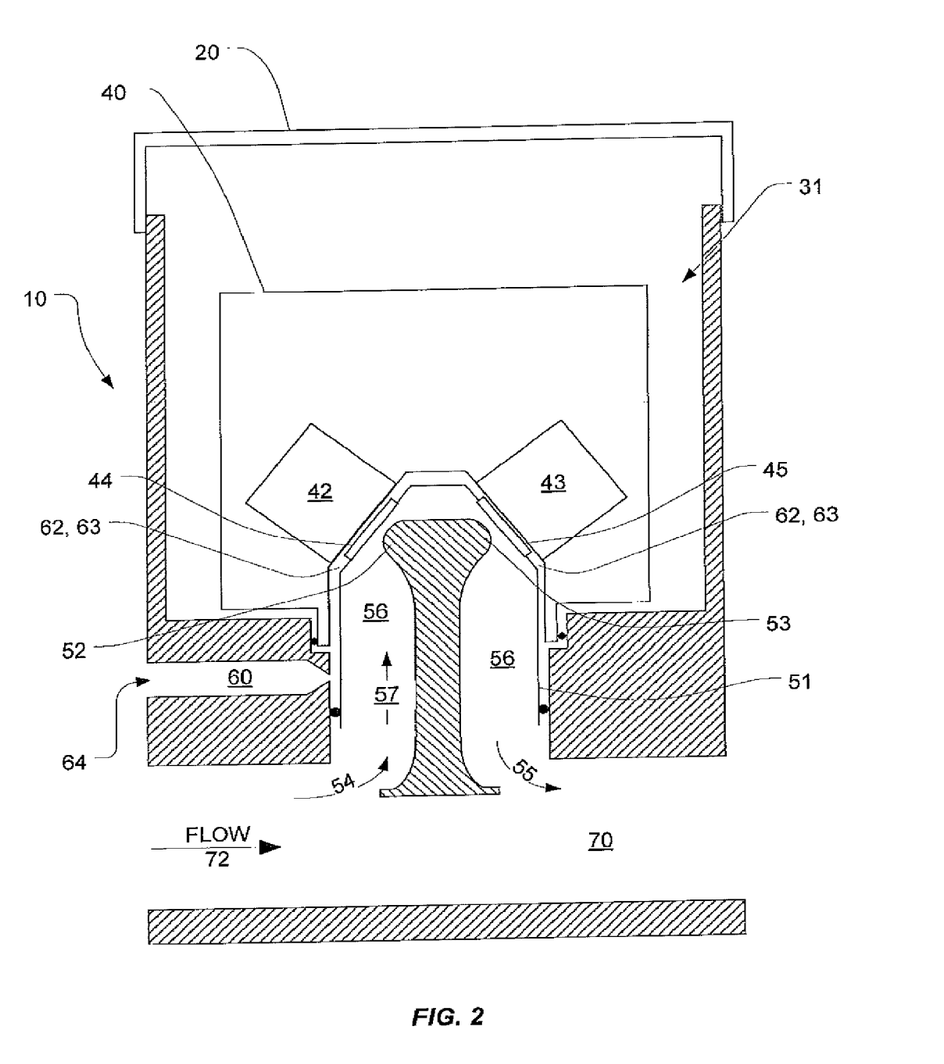
FIG. 2 illustrates a cross-section taken through the embodiment of FIG. 1 showing the internal arrangement of the gas detectors, membranes and flow control structures.

FIG. 2 shows a schematic cross-sectional view showing more internal detail (as will be discussed later) and further demonstrating the interaction with the bulk gas duct 70. As can be seen in FIG. 2 the gas detector apparatus 10 comprises the following main components:

A main housing 30 defining an internal compartment 31 in which the components of the detector are housed. At a first end the housing 30 defines a duct 70 in which bulk gas flows in use. This duct can be connected during installation to a further pipe or duct of an air delivery system, or may indeed be part of an air delivery system.

A lid 20 which closes the top of the main housing 30. The lid 20 closes the top of the housing 30 and is removable from the housing 30 to enable components of the gas detection apparatus 10 to be serviced, replaced or exchanged as required.

A central insert 50 which extends into the duct 70 and provides a scoop-like structure (the sample inlet 54) to direct a sample flow into a sample passage 56 defined within the detector apparatus. The downstream side of the central insert 50 defines an outlet port (the sample outlet 55) into the duct 70 to exhaust the air sample back into the duct 70 after analysis. The pressure drop across the inlet and outlet formed by the central insert and the insert's protrusion into the duct 70 are sufficient to draw air through the sample passage 56 without an additional fan.

The central insert 50 also defines at least part of an inner wall of the sample passage in which a sample flows and provides in this example flow control structures, e.g. deflectors 52 and 53, to set up a desired air flow characteristic in the passage 56.

The central insert 50 is removable from the apparatus 10 for cleaning or changing, and can preferably be inserted into main housing 30 either from below (if no bulk gas duct 70 is present) or above (when detector cartridge 40 is absent).

A passage defining insert 51. The passage defining insert 51 is removably mounted in a recess in the main housing 30 and cooperates with the central insert 50 to define the sample passage 56. The passage insert 51 includes one or more apertures that are closed by membranes 44 and 45 through which gas diffuses during operation. The passage defining insert 51 is mounted to the housing and sealed around its periphery by an o-ring.

A gas detector cartridge 40 that contains one or more gas sensors 42 and 43 and is removably mounted within the main housing 30. The detector cartridge 40 is removable and interchangeable to enable servicing swapping or upgrading of the detectors housed therein. The gas detector cartridge 40 is mounted such that it is spaced apart from the passage defining insert 51 to provide a test region 62 between the membranes 44, 45 and gas detectors 42, 43 of the gas detector cartridge 40. The housing is also provided with a test inlet 60 that is in fluid communication with test region 62 to introduce calibration gas into the test region 62. The gas detector cartridge is sealed against the housing 30 with an o-ring.

The gas detectors 42 or 43 can be any known in the art. For instance, the gas detector may be one for detecting the presence of at least one target species' such as 8O2, NO2, CL2, CL02, CO2, NH3, HCl, HCN, NO, 02, H2, CO, H2S or CH4. Other volatile organic compounds (VOCs), as would be known in the art, may also be a target species. Different gas detectors are known to be responsive to different gases. Suitable detector types might be electrochemical sensors, catalytic diffusion sensors, explosimeters, infrared point sensors, non-dispersive infrared sensors, solid state metal oxide semiconductors, and/or photo ionization detectors.

In use, bulk gas 72 flows in bulk gas duct 70. As the bulk gas reaches sample inlet 54, a portion is redirected into the sample passage 56 to become sample gas 57. The sample gas 57 is drawn towards deflector 52 in a first flow direction. Upon encountering deflector 52, at least a portion of the sample gas 57 is redirected to have a different second flow direction. This second flow direction is towards the membrane 44. Then, a portion of sample gas 57 and any target species within it will pass through membrane 44, and enter test region 62. From there, the gas mixture is able to interact with the gas detector 42 (the exact nature of the interaction will depend on the type of detector) and any target species in the gas mixture will be detected.

Flow can be described by, among other things, streamlines, streaklines and pathlines; a streamline is a curve that is instantaneously tangent to the velocity vector of the flow, a streakline is the locus of all gas molecules that have passed through a particular spatial point over a certain time frame, and a pathline is the trajectory that an individual gas molecule will have. In laminar flow through a pipe, (i) streamlines, streaklines and pathlines are the same, (ii) a boundary layer exists where velocity along the pipe approaches zero, and (iii) high momentum diffusion, but low momentum convection, occurs in the direction towards the surfaces of the pipe. In turbulent flow through a pipe mixing is increased significantly and (i) streamlines, streaklines and pathlines are not the same, (ii) a relatively larger boundary layer, which is not well understood, exists, and (iii) high momentum convection, but low momentum diffusion, occurs in the direction towards the surfaces of the pipe. An increase in velocity, among other things, leads to a transition from laminar flow to turbulent flow.

Imagine a flow in a sample passage. In any cross-section of the flow, the majority of molecules will be moving in the bulk direction along the sample passage. However, some molecules will also be moving towards the surface(s) defining the sample passage (ie across the bulk direction of flow) by way of 'passively occurring' momentum diffusion (predominantly in the case of laminar flow) and 'passively occurring' momentum convection (predominantly in the case of turbulent flow). By 'passively occurring' it is meant that the flow directions are not as a result of the flow control structure of the present invention. Such 'passively occurring' momentum diffusion and momentum convection are not "towards the membrane" as it is to be understood in this invention. Instead, in this invention, "towards the membrane" should be understood to mean 'flow control structure derived' momentum diffusion, momentum convection and/or bulk flow direction.

Flow in the bulk direction, i.e. along the sample passage, may be considered towards the membrane if a flow control structure is use to change the net bulk flow direction in a position proximate to the membrane. For instance, if the sample passage comprises an elbowed pipe and the membrane is positioned on the outside of the elbow of the pipe, flow in the pipe (whether laminar or turbulent) is aimed towards the membrane at the elbow, hits the membrane at the elbow, and is then redirected around the corner formed by the elbow. The flow is 'flow control structure derived' since the pipe directs the bulk flow direction at the membrane in the elbow. If the membrane is not positioned at the elbow, and is instead simply positioned in a wall parallel to the direction of bulk flow at a position where no change in net flow direction is being induced, and there is otherwise no flow control structures present, there will be only 'passively occurring' diffusion and convection of sample gas molecules in a direction transverse to the bulk direction of flow (i.e. towards the membrane). In this situation, a flow control structure resulting in a second bulk flow direction, i.e. a 'flow control structure derived' flow, that is towards the membrane is required.

Without wishing to be bound by theory, such 'flow control structure derived' flow towards the membrane is believed to be greater than would occur in 'passively occurring' flow. Accordingly, the flow control structure of the present invention is one which provides for greater flow towards the membrane than would occur in (i) laminar flow conditions by momentum diffusion (predominantly) or (ii) turbulent flow conditions momentum convection (predominantly), and thus is one which enhances the passage of the sample gas and entrained target species through the membrane.

In order to achieve suitable flow conditions in the sample flow surrounding the membranes 44 and 45, various flow control structures could be substituted for the bulbs 52 and 53 of the insert 50. For example an angled deflector that is separated from the central insert 50 and sample passage defining insert 51 could be provided.

The remainder of the sample gas 57 that does not pass through membrane 44 to detector 42 continues in sample passage 56. A similar scenario may occur at membrane 45 and detector 43, where the same, or an alternative target species, can be tested for. Then, any remaining sample gas 57 passes out of the gas detector apparatus 10 via sample outlet 55 and back into the bulk gas duct 70.

For calibration and/or back-flushing of membrane 44 and 45, calibration gas is fed into test region 62 through test inlet 60. For calibration, the test gas 63 will be calibration gas. For backflushing alone, the test gas 63 could be calibration gas (although this is usually expensive) or simply flush gas (e.g. ambient or preferably filtered air).

To perform calibration, the system requires a source of calibration gas, e.g. a gas bottle(s) with suitable pressure regulator(s), to be attached to the test inlet 60, e.g. via calibration port 64 through a solenoid valve(s). In the test inlet 60 there is located a duckbill valve, e.g. made of an elastomeric material, which prevents gas returning to the test inlet 60 from the test region 62 if several devices are being calibrated simultaneously. The calibration gas delivery system is periodically activated by energizing the solenoid valve(s) to inject the required zero or span calibration gas for each sensor type. Calibration cycles can be controlled by either internal or external means, and may be either automatic, e.g. operate on a predetermined schedule or when certain performance criteria are fulfilled, or alternatively, performed on demand in response to a user input.

The alarms during this period are inhibited and suitable time delays are introduced to allow the sensor to settle. During calibration the calibration gas 63 floods the test region 62 and exits through the membranes 44 and 45. This action also serves to back-flush these membranes. The readings from each sensor at the time of calibration are stored and used subsequently to adjust the sample readings.

The solenoid is then shut off to allow the sample gas 57 to again diffuse through the membranes 44 and 45 from the sample chamber 56 and fill the test region 62. The test region 62 is configured to have low dead volume for fast response.

Figure 6:
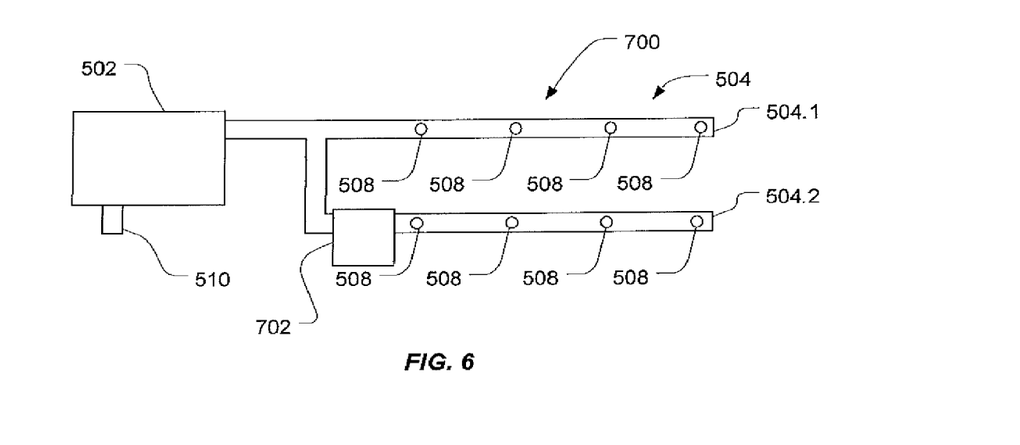
FIG. 6 illustrates a second embodiment of an air sampling pollution monitoring system that has been augmented with a gas detection apparatus according to an embodiment of the present invention.
Figure 9:
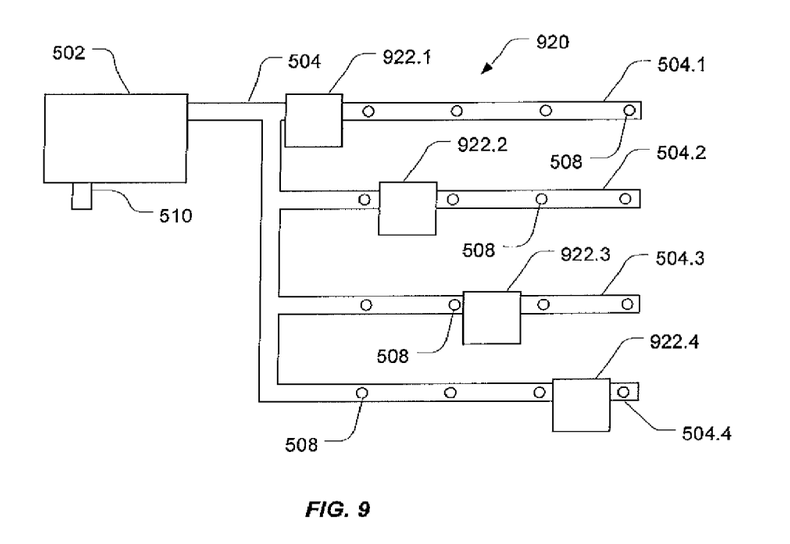
FIG. 9 illustrates a further embodiment of an air sampling pollution monitoring system according to an embodiment of the present invention that includes a plurality of gas detection apparatuses.
Figure 10:
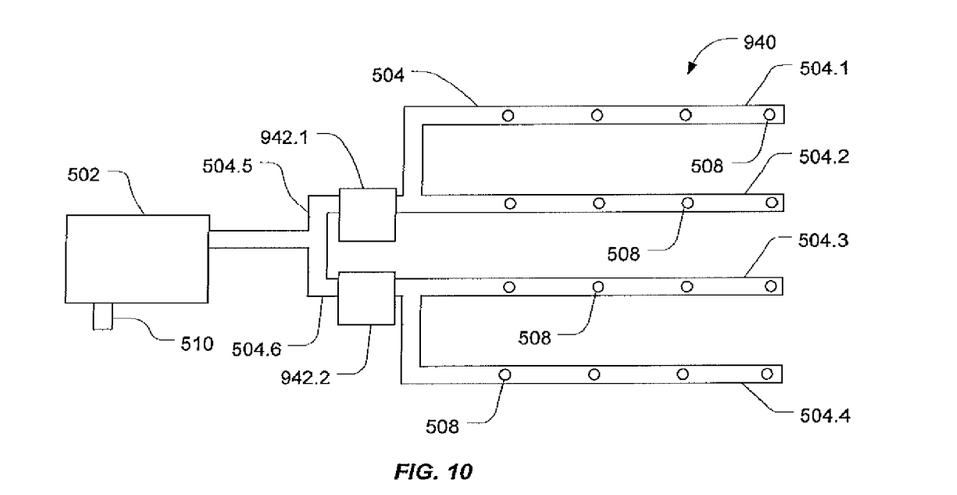
FIG. 10 illustrates another embodiment of an air sampling pollution monitoring system according to an embodiment of the present invention that includes a plurality of gas detection apparatuses.

The arrangement of components described above preferably provides a sealed airflow path that returns all sample gas back to the bulk flow in the duct 70. Advantageously this makes the detector of this embodiment particularly suited for installation in an air sampling duct of a particle detection system in a position upstream of the particle detector, e.g. as illustrated in the examples of FIGS. 6, 9 and 10, because no sample air is lost from the system via leakage from the gas detection apparatus. Clearly such a gas detection apparatus can also be used on the exhaust of a particle detector.

Figure 3:
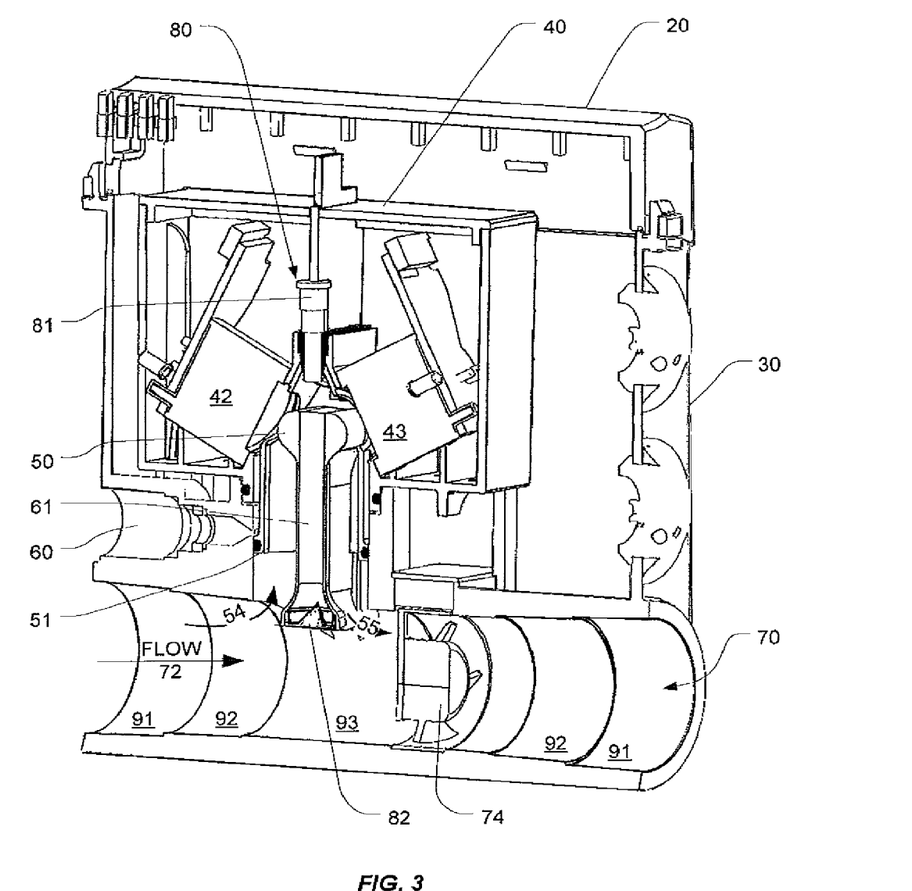
FIG. 3 illustrates a perspective cross-section taken across a second embodiment of the gas detector apparatus showing the internal arrangement of the gas detectors, membranes and flow control structures.

The embodiment of FIG. 3 is similar to that of FIG. 2 except that it additionally includes an optional nephelometer 80, e.g. a photo-electric smoke detector and a fan 74.

The nephelometer 80 includes a light source 81. Preferably the light source is a laser (e.g. about 5 mW) or LED light source, adapted to emit a light beam across the top of sample passage 56 and along a channel 61 defined in the center of the central insert 50. A light receiver (not shown), e.g. Si photodiode or similar, is placed off axis with respect to the beam and receives light that is scattered from particles, e.g. smoke entrained in the sample flow 57. To minimize stray reflections the channel 61 is terminated in a beam dump formed by an angled reflector 82, which prevents return reflections impinging on the photodiode of the nephelometer 80.

The fan 74 mounted in the bulk gas duct 72 is included in embodiments where an existing flow of bulk gas is not present, e.g. in stand alone systems or systems where external flows are low. The sample passage 56 may also be flushed by intermittently operating the fan 74, or a further fan not shown, at a rate high enough to cause flushing. The power for this intermittent operation of the fan, or intermittent increase speed of the fan, may be taken from an addressable fire alarm loop.

Operation of the gas detector may be user-controlled, intermittent or continuous. In order to minimize power draw intermittent operation may be preferred. In a preferred embodiment, electrical power for the system is taken from a fire alarm loop, either directly by the apparatus 10, or via an associated particle detections system, if the gas detection apparatus is used to augment such a system.

In this example, the duct 70 of the gas detection apparatus includes has a stepwise narrowings from its edge to center. In this example the outermost portions 91 of the duct 70 have a relatively large diameter compared to inwardly adjacent portions 92 of the duct 70, which have a narrower inside diameter. The central portion 93 is narrower still. This stepped arrangement facilitates installation, particularly when retrofitting to existing particle detection systems because it allows identical gas detection apparatuses to be fitted to different particle detection system, which have air sampling ducts with different outside diameters. The steps between adjacent segments in the duct can also act as a depth stop so that during installation the air sampling duct is not inserted so far into the duct 70 of the gas detection apparatus that the main air sampling duct does not interfere with the entry of air into the airflow path 56 of the gas sensing apparatus. A tapered duct could also be used.

Figure 4:
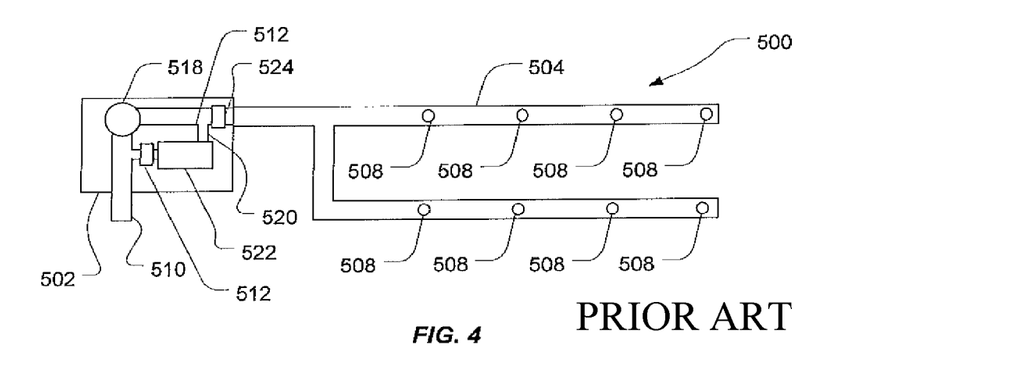
FIG. 4 illustrates a conventional air sampling pollution monitoring system.

FIG. 4 illustrates a conventional air sampling particle detection system 500. The system 500 includes the particle detector 502 coupled to a duct in the form of a sample pipe network 504. The sampling pipe network includes a plurality of air sample inlets 508. In use, air is drawn into the air sample inlets 508 and into the particle detector 502 via an aspirator which typically forms part of the particle detector 502. Air drawn through the system 500 is exhausted back to the atmosphere via an exhaust port 510.

The particle detector 502 in this example includes an airflow flow path 512 between its inlet 514 and exhaust port 510. An air sample is drawn from the environment begin monitored, along the air sampling duct and into detector flow path 512 by an aspirator 518. A part of this air sample flow is then drawn into an analysis airflow path 520 where is enters a particle detection chamber 522. Air passing through the detection chamber 522 is analyzed to determine a level of particles in the air. In response to the level of particles detected and possibly other criteria the detector is configured to generate an output according to alarm and or fault logic applied by its controller.

The detector 502 can also include additional components, including but not limited to a flow sensor 524 that is used to determine the flow rate of air passing through the particle detector, a filter 526 which serves to remove unwanted particles, e.g. dust etc. from the air flow to minimize or prevent soiling of the interior of the detection chamber 522 over time.

The detection chamber 522 can operate using any particle detection principle, including but not limited to, light scattering, light obscuration, ionization etc. For example the particle detector could be a VESDA LaserPLUS detector from Xtralis Pty Ltd. or ICAM IAS detector also from Xtralis Pty Ltd, or some other detector.

FIGS. 5 to 8 illustrate several uses of a gas detection apparatus of an embodiment of the present invention.

The type of air sampling particle detection system shown in FIG. 4 can be augmented by using a gas detection apparatus made in accordance with the embodiment of the present invention. FIGS. 5, 6, 9 and 10 show two of the various ways in which a particle detection system similar to that of FIG. 4 can be set up to include a gas detecting apparatus. In these figures, common features to the system illustrated in FIG. 4 will share common reference numerals.

Figure 5:
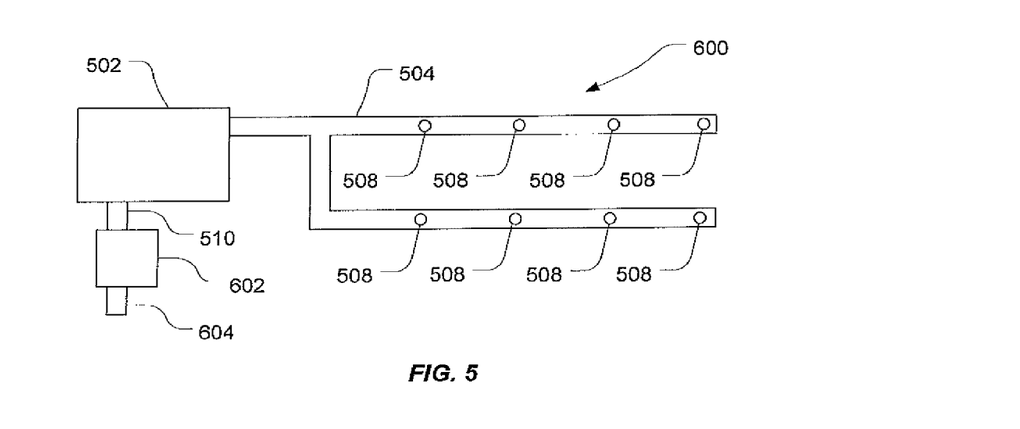
FIG. 5 illustrates a first embodiment of an air sampling pollution monitoring system that has been augmented with a gas detection apparatus according to an embodiment of the present invention.

FIG. 5 shows an air sampling particle detection system 600 including a particle detector 502 in fluid communication with a sampling pipe network 504. In this example, the exhaust 510 of the particle detector 502 is coupled to a gas detecting apparatus 602 of the type described above. The air which is expelled from the exhaust of the particle detector 502 passes into the gas detector 602 before finally being sent back to atmosphere via its exhaust 604.

FIG. 6 illustrates an example of a preferred form of the present invention. In this example, the underlying smoke detection system is generally the same as that of FIG. 4. However, the sample pipe network 504 has a gas detector 702, as described above, positioned upstream from the particle detector along one of its branches. In this regard, air from a first branch 504.1 of the sampling pipe network 504 is drawn directly into the particle detector 502 whereas air drawn into the second branch 504.2 of the sample pipe network 504 first passes through gas detector 702 for gas analysis prior to passing to the particle detector 502. Such an embodiment may be useful in situations where localized gas release is possible. For example, in a warehouse with a refrigerant unit at one end, it may be necessary to monitor the entire space for smoke using the particle detector. However, detecting refrigerant leaks is only necessary in the area adjacent the refrigeration unit and thus, providing a relatively local gas detector unit such as that 704 is advantageous.

FIGS. 9 and 10 illustrate two further exemplary particle detection systems that include gas detection apparatuses in them. Turning firstly to FIG. 9 there is illustrated a particle detection system 920 which includes an aspirated particle detector 502 as described above. The particle detector 502 is connected to an air sampling network 504, which includes four branches 504.1, 504.2, 504.3 and 504.4, each of which have a plurality of sampling points or holes 508 into which air is drawn. Each branch of the duct work 504.1, 504.2, 504.3 and 504.4 includes its own gas detection apparatus, 922.1, 922.2, 922.3 and 922.4. Each gas detection apparatus 922.1, 922.2, 922.3 and 922.4 could be sensitive to the same or different target species, depending on the nature of the installation. Importantly each gas detection apparatus 922.1, 922.2, 922.3 and 922.4 will receive air from a respective subset of the sampling holes 508 of the system. In this case, the subset of sampling points upstream of each of the gas detection apparatuses 922.1, 922.2, 922.3 and 922.4 has a different number of air sampling holes up stream of it. This has implications for sensitivity (to samples drawn through each sampling hole) and therefore calibration or the detectors or setting of detection and/or alarm thresholds for each detector.

FIG. 10 illustrates another particle detection system 940. The particle detector 502 is connected to an air sampling network 504 which includes a tree-like structure. The network 504 has two intermediate branches 504.5 and 504.6 which subsequently branch into four branches 504.1, 504.2, 504.3 and 504.4, each of which have a plurality of sampling points or holes 508 into which air is drawn. Each of the intermediate branches 504.5 and 504.6 of the duct work 504 includes a gas detection apparatus, 942.1 and 942.2. As will be appreciated each gas detection apparatus receives air drawn through a respective subset of 8 sampling points located upstream of it.

A factor which needs to be accounted for when commissioning a system such as those of FIGS. 5 and 6 is that differences in calibration of the gas detecting units 602 and 702 will be necessary. This is largely due to the difference in dilution ratios that exist in these two systems. In the system of FIG. 5, air drawn through any of the eight sampling holes of the sample pipe network 504 will pass through the gas detector 602. Thus, if gas is entering any one of the sample holes it will be diluted by a ratio of 7:1 by the air entering the entire set of sampling holes in the sample pipe network 504. In contrast, in FIG. 6, any gas entering the holes in the second arm 504.2 of the sample pipe network 504 will be diluted by only 3:1. In this case different gas detection thresholds and saturation thresholds will need to be set in the gas detection apparatus 602 and 702.

Accordingly, one aspect of the present invention provides software for automatically determining calibration values for a gas detector based on one or more system characteristics, e.g. the configuration of a sampling network to which it is attached, the location in which the system is installed, and/or the likely sources of gas nearby the system.

The software may operate in a manner similar to flow modelling software used in aspirated particle detection systems, e.g. Aspire from Xtralis Pty Ltd.

For example the software is configured to calculate alarm thresholds for a gas alarm in a particular system configuration. Where the system dilutes gas samples, the threshold calculation is based on compensation for the dilution introduced by the sampling network.

Compensation for gas distribution is also performed, such that application specific parameters are accounted for, For instance in a car park the CO distribution is homogenous and therefore a similar level of gas is introduced into every sample hole. In such cases the compensation of the alarm threshold is not required.

The results of the alarm threshold analysis can be presented as a file for the operator to configure the instrument or can be directly downloaded into the detection equipment. Alarms can be set in a centralized controller or distributed at each sensor.

The sealed configuration of the gas detection apparatus of the preferred embodiment allows the gas detection apparatus to form part of the upstream portion of the duct of the particle detection system without disadvantage in terms of pressure, leakage or transport time.

Figure 7:
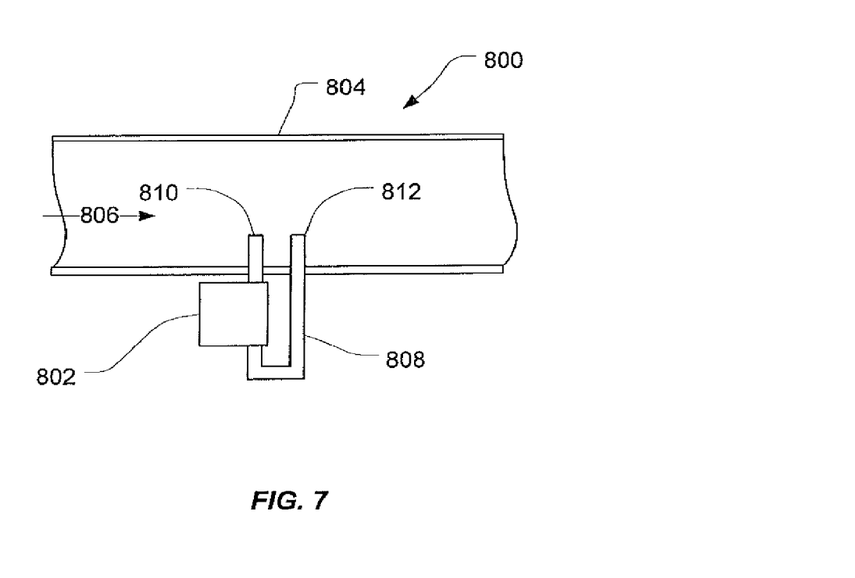
FIG. 7 illustrates a gas detection apparatus according to an embodiment of the present invention mounted on a duct of a heating, ventilating, and air conditioning (HVAC) system.

FIG. 7 illustrates a further embodiment of a gas detector of the present invention but this time it is mounted on a duct of an HVAC system. In this example, the gas detecting system 800 comprises a gas detector 802 mounted to an HVAC duct 804 in which air is flowing in direction of arrow 806. The gas detector 802 is provided with a duct probe 808 which has an upstream inlet 810 and a downstream outlet 812. The pressure difference across the inlet and outlet 810 and 812 sucks air through the gas detector 802 for analysis.

Figure 8:
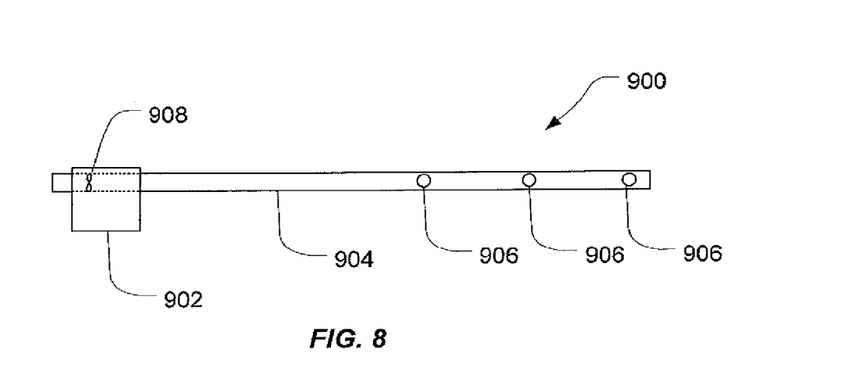
FIG. 8 illustrates a stand alone aspirated embodiment of a gas detection apparatus according to the present invention.

FIG. 8 shows a further embodiment of a gas analysis system made in accordance with an embodiment of the present invention. This system 900 includes a gas detector 902 coupled directly to a sampling pipe 904 which has a plurality of sampling holes 906. In this embodiment, no separate particle detector is provided. However, the gas detector 902 may be provided with an internal particle detection system such as that described above. In this system it will be necessary to draw air through the sample pipe 904 to the gas detector 902. To this end, the gas detector 902 is provided with a fan 908 to draw air into it.

Referring again to FIGS. 2 and 3, the output from the gas detectors 42 and 43, and optional nephelometer 80, can be processed either alone or in combination by one or more onboard data processing systems, e.g. a microprocessor based control system, or transmitted to an external data processing system to determine whether an abnormal condition exists in the volume being monitored. In this regard, the processing system will apply alarm and or fault logic, as known to those skilled in the art, to determine if either an abnormal gas detection event, smoke detection event, fault or other event has occurred, and whether an action e.g. raising an alarm, increasing an indicated threat level, setting off suppression systems, closing down operations of certain plant and equipment etc. needs to be performed.

The structure of the gas detector apparatus can be made with suitable materials so as to be explosion proof or to configure it for use in an explosion risk zone. Additionally, internal components could be potted with suitable compound to prevent a flame to propagate out. In such an embodiment the membranes 44 and 45 in this case would preferably be flame arrestors, for example made from sintered material of a suitable type and thickness to prevent a flame propagating from the control electronics and detectors in to the sample passage 56. Moreover, because a gas detector of this type has very low power demands it is possible for the detector to be made intrinsically safe, so that it can be used in hazardous areas. This is particularly the case for embodiments that do not include a separate aspirator or nephelometer, e.g. the embodiment illustrated in FIG. 2.

It will be understood that the invention disclosed and defined in this specification extends to all alternative combinations of two or more of the individual features mentioned or evident from the text or drawings. All of these different combinations constitute various alternative aspects of the invention.

What is claimed is:

1. A system for detecting a condition in an environment, the system including:
    a particle detector arranged to detect the presence of particles in an air sample;
    a sampling pipe network including a plurality of air sample inlets in fluid communication with the environment and the particle detector;
    an aspirator to draw an air sample from the environment to the particle detector through the sampling pipe network; and
    and at least one gas detection apparatus having a housing and being arranged in fluid communication with the sampling pipe network at a location upstream of the particle detector, and at least one gas detector sensitive to a target species; said gas sensor being arranged to detect the presence of the target species in at least part of the air sample flowing in the sampling pipe network.

2. The system as claimed in claim 1 wherein the housing includes a duct portion.

3. The system as claimed in claim 2 wherein the sampling pipe network includes at least one air sampling pipe including a plurality of air sample inlets arranged in series along the duct portion, said gas detection apparatus being arranged to take a sub-sample from the air sampling pipe downstream of at least two air sample inlets and being calibrated with a dilution factor reflecting a diluting effect of the plurality of sample inlets on the air sampling pipe upstream of the gas detection apparatus.

4. The system as claimed in claim 3 which includes at least two gas detection apparatuses, each gas detection apparatus being arranged to take a sub-sample from an air sampling pipe at a respective position and being calibrated with a corresponding dilution factor reflecting a diluting effect of the sample inlets of the air sampling pipe upstream of the gas detection apparatus's respective position.

5. The system as claimed in claim 1, wherein said gas detection apparatus further includes:
    an inlet port arranged to draw a sub-sample from the air sample flowing in sampling pipe network for analysis by the gas detection apparatus;
    an outlet port arranged to exhaust the sub-sample of air;
    a flow path extending from the inlet port to the outlet port, and
    at least one gas detector sensitive to a target species arranged in fluid communication with the flow path to detect the presence of the target species in the sub-sample.

6. The system as claimed in claim 5 wherein said gas detection apparatus further includes:
    a sample passage defining the flow path and including:
        a test region; and
        at least one membrane providing fluid communication between the sample passage and the test region such that a target species in the sample is capable of passing through the membrane and into the test region; and
    wherein the sample passage includes a flow control structure to direct at least a portion of the sample gas towards the membrane.

7. The system as claimed in claim 6 wherein the flow control structure defines a curve in the sample passage and said membrane is located on an outside portion of the curve.

8. The system as claimed in claim 6, wherein the flow control structure includes any one or more of
    (i) a narrowing of the sample passage;
    (ii) a bulbous protrusion from a surface defining a wall of the sample passage;
    (iii) a baffle extending into the sample passage from at least one of the surface defining the sample passage; and
    (iv) an object within the sample passage obstructing the sample flow.

9. The system as claimed in claim 1 wherein the inlet port and outlet port of said gas detection apparatus are positioned in the airflow in the duct portion of the housing or the sampling pipe network such that a pressure drop between the inlet port and outlet port serves to draw air through the flow path.

10. The system as claimed in claim 1 which further includes means to draw air into the input port of said gas detection apparatus.

11. The system as claimed in claim 1 which further includes a secondary gas inlet configured to provide a calibration gas to the test region of said gas detection apparatus.

12. The system as claimed in claim 11 wherein gas provided by the secondary gas inlet to the test region is flushed from the test region through one or more associated membranes into the flow path.

13. The system as claimed in claim 1 wherein the further including particle detection apparatus arranged to detect the presence of particles in the flow path of said gas detection apparatus.

14. The system as claimed in claim 1, wherein the sampling pipe network includes at least two air sample inlets arranged to draw air samples from respective portions of the environment, and wherein the system further includes at least two gas detection apparatuses being sensitive to at least one target species to be detected in an portion of the environment proximate the a respective air sample inlet.

15. The system as claimed in claim 14 in which at least two gas detection apparatuses are positioned with respect to the sampling pipe network such that each gas detection apparatus is able to draw a sub-sample from the duct portion including an air sample flow drawn from a corresponding subset of air sample inlets which are not the same.

16. The system as claimed in claim 15 in which the subset of air sample inlets corresponding to one gas detection apparatus differs by at least one air sample inlet to the subset of air sample inlets of another particle detection apparatus.

17. The system as claimed in claim 16 in which the subset of air sample inlets corresponding to one gas detection apparatus does not include any air sample inlets that form part of the subset of air sample inlets corresponding to another particle detection apparatus.

18. The system as claimed in claim 14 wherein the at least two gas detection apparatuses are sensitive to at least one different target species.

19. The system as claimed in claim 1 wherein the gas detection apparatus includes any one or more of:

an explosion proof housing;

one or more flame arrestors; and intrinsically safe electrical circuitry.

20. The system as claimed in claim 19 which further includes an intrinsically safe particle detector.

21. The system as claimed in claim 20 which includes a barrier device for providing electrical power to the intrinsically safe particle detector.

\* \* \* \* \*

UNITED STATES PATENT AND TRADEMARK OFFICE
CERTIFICATE OF CORRECTION

| | |
|---|---|
| PATENT NO. | : 9,618,440 B2 |
| APPLICATION NO. | : 14/931339 |
| DATED | : April 11, 2017 |
| INVENTOR(S) | : Williamson |

It is certified that error appears in the above-identified patent and that said Letters Patent is hereby corrected as shown below:

Column 9, Lines 42-44, delete "802, NO2, CL2, CL02, CO2, NH3, HCl, HCN, NO, 02, H2, CO, H2S or CH4." and insert --$SO_2$, $NO_2$, $Cl_2$, $ClO_2$, $CO_2$, $NH_3$, HCl, HCN, NO, $O_2$, $H_2$, CO, $H_2S$ or $CH_4$.-- therefor Column 11, Line 66, delete "flow" and insert --gas-- therefor Column 15, Line 54, in Claim 1, before "at least", delete "and"

Signed and Sealed this
Twenty-eighth Day of April, 2020

Andrei Iancu
*Director of the United States Patent and Trademark Office*